US010292612B2

(12) United States Patent
Osypka et al.

(10) Patent No.: US 10,292,612 B2
(45) Date of Patent: May 21, 2019

(54) ELECTRO-PHYSIOLOGY MAPPING CATHETER LOOP HAVING ATRAUMATIC TIP SECTION

(71) Applicant: Oscor Inc., Palm Harbor, FL (US)

(72) Inventors: Thomas P. Osypka, Palm Harbor, FL (US); Timothy A. Searfoss, New Port Richey, FL (US)

(73) Assignee: Oscor Inc., Palm Harbor, FL (US)

( * ) Notice: Subject to any disclaimer, the term of this patent is extended or adjusted under 35 U.S.C. 154(b) by 335 days.

(21) Appl. No.: 15/259,853

(22) Filed: Sep. 8, 2016

(65) Prior Publication Data

US 2017/0065226 A1 Mar. 9, 2017

Related U.S. Application Data

(60) Provisional application No. 62/215,434, filed on Sep. 8, 2015.

(51) Int. Cl.
*A61B 5/042* (2006.01)
*A61B 5/00* (2006.01)
(52) U.S. Cl.
CPC .......... *A61B 5/0422* (2013.01); *A61B 5/6856* (2013.01)
(58) Field of Classification Search
CPC ..................... A61B 5/0422; A61B 5/6856
See application file for complete search history.

(56) References Cited

U.S. PATENT DOCUMENTS

| 6,325,797 | B1* | 12/2001 | Stewart | A61B 18/1492 606/41 |
| 6,514,246 | B1* | 2/2003 | Swanson | A61L 31/10 600/374 |
| 6,702,811 | B2* | 3/2004 | Stewart | A61B 18/1492 606/41 |
| 8,728,065 | B2* | 5/2014 | Fish | A61B 5/0422 600/374 |
| 8,731,631 | B2* | 5/2014 | Kim | A61B 5/0422 600/374 |
| 2010/0069733 | A1* | 3/2010 | Kastelein | A61B 5/042 600/374 |
| 2011/0092789 | A1* | 4/2011 | Jung | A61B 5/0422 600/374 |

FOREIGN PATENT DOCUMENTS

JP WO2013145891 * 10/2013

* cited by examiner

*Primary Examiner* — Lee S Cohen
(74) *Attorney, Agent, or Firm* — Locke Lord LLP; Scott D. Wofsy

(57) ABSTRACT

An electro-physiology mapping catheter is disclosed which includes an elongated body having opposed proximal and distal end portions and defining a longitudinal axis therebetween, the distal end portion of the body forming a generally circular mapping loop that extends through a plane oriented generally perpendicular to the longitudinal axis of the elongated body, the circular mapping loop having an inwardly bent distal tip section.

2 Claims, 4 Drawing Sheets

ELECTRO-PHYSIOLOGY MAPPING CATHETER LOOP HAVING ATRAUMATIC TIP SECTION

CROSS-REFERENCE TO RELATED APPLICATION

The subject invention claims the benefit of and priority to U.S. Provisional Application Ser. No. 62/215,434 filed Sep. 8, 2015, the disclosure of which is herein incorporated by reference in its entirety.

BACKGROUND OF THE INVENTION

1. Field of the Invention

The subject invention is directed to an endocardial diagnostic device, and more particularly, to an electro-physiology mapping catheter having a distal mapping loop with an atraumatic tip portion designed for use within the pulmonary vein.

2. Description of Related Art

Cardiac arrhythmia occurs when regions of cardiac tissue abnormally conduct electrical signals to adjacent tissue, which disrupts the normal cardiac cycle and causes asynchronous rhythm. The primary sources of such signals are located in the tissue region that extends along the pulmonary veins of the left atrium and in the superior pulmonary veins. After unwanted signals are generated in the pulmonary veins or conducted through the pulmonary veins from other sources, they are conducted into the left atrium where they can initiate or continue arrhythmia.

Procedures for treating arrhythmia are well known and include surgically disrupting the origin of the signals causing the arrhythmia, as well as disrupting the conducting pathway for such signals. It has been found that by mapping the electrical properties of the endocardium and the heart volume, and selectively ablating cardiac tissue by application of energy, it is possible to stop or modify the propagation of unwanted electrical signals from one portion of the heart to another. Tissue ablation can be used to destroy the unwanted electrical pathways by formation of non-conducting lesions.

Typically this involves a two-step procedure that includes mapping followed by ablation. Mapping electrical activity at points in the heart is typically sensed and measured by advancing a mapping catheter containing one or more electrical sensors into the heart, and acquiring data at a multiplicity of points. The data is then utilized to select the target areas where ablation is to be performed.

The shape of the mapping catheter can vary depending upon the tissue being mapped. For example, to map the pulmonary vein, the catheter can be shaped as a continuous loop, as illustrated in FIG. 1. In use, when the prior art mapping catheter loop of FIG. 1 is inserted into the pulmonary vein for mapping and the catheter shaft is rotated counter-clockwise, the tip of the mapping loop can catch onto, and perforate the pulmonary vein. If counter-clockwise rotation is continued for one full turn after penetration of the pulmonary vein, the mapping catheter loop can physically exit the interior of the pulmonary vein and wrap itself around the exterior of the pulmonary vein.

After such an event has occurred, the application of subsequent clockwise rotation of the loop may not be effective to pull the loop back inside the pulmonary vein. This can present a situation where the mapping loop cannot be retrieved from the pulmonary vein, and successive retrieval attempts can produce hemorrhaging, putting the patient at risk.

To prevent contact of the mapping catheter loop tip to the pulmonary vein, the improved configuration of the subject invention incorporates a bend of the loop and an extension toward the center of the loop away from contact with the pulmonary vein. As a result of this design, counter-clockwise rotation of the loop while inside the pulmonary vein will not present contact of the tip to the pulmonary vein preventing pulmonary vein perforation.

Moreover, the improved loop configuration of the subject invention does not allow the tip of the loop to come in contact with the pulmonary vein, as the tip is protected by the surrounding loop from pulmonary vein contact. The extension of the tip to the center of the loop also reduces the strength of the tip if the loop comes into contact with heart tissue in a flat, face forward orientation. Furthermore, if this occurs, the tip section will deflect away and not penetrate the heart tissue.

SUMMARY OF THE INVENTION

The subject invention is directed to a new and useful electro-physiology mapping catheter that includes an elongated body having opposed proximal and distal end portions and defining a longitudinal axis there between. The distal end portion of the body forms a generally circular mapping loop that extends through a plane oriented generally perpendicular to the longitudinal axis of the elongated body. The circular mapping loop has an inwardly bent distal tip section.

The inwardly bent distal tip section is bent radially inward toward a center of the circular mapping loop. The inwardly bent distal tip section is lying generally within the plane of the circular mapping loop. Preferably, the circular mapping loop has an arcuate length that is greater than about 360 degrees. More preferably, the circular mapping loop has an arcuate length that is less than about 450 degrees.

The circular mapping loop includes a plurality of spaced apart electrode bands, and the inwardly bent distal tip section of the mapping loop includes an atraumatic distal tip. A central bore extends through the body of the catheter from the proximal end thereof toward the distal end thereof to accommodate a stylet for maintaining the circular mapping loop in a generally straightened configuration during vascular introduction. A handle assembly operatively associated with the proximal end portion of the catheter body.

These and other features of the mapping catheter of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the mapping catheter of the subject invention without undue experimentation, preferred embodiments thereof will be described in detail herein below with reference to certain figures, wherein.

DETAILED DESCRIPTION OF PREFERRED EMBODIMENTS

Figure 1:
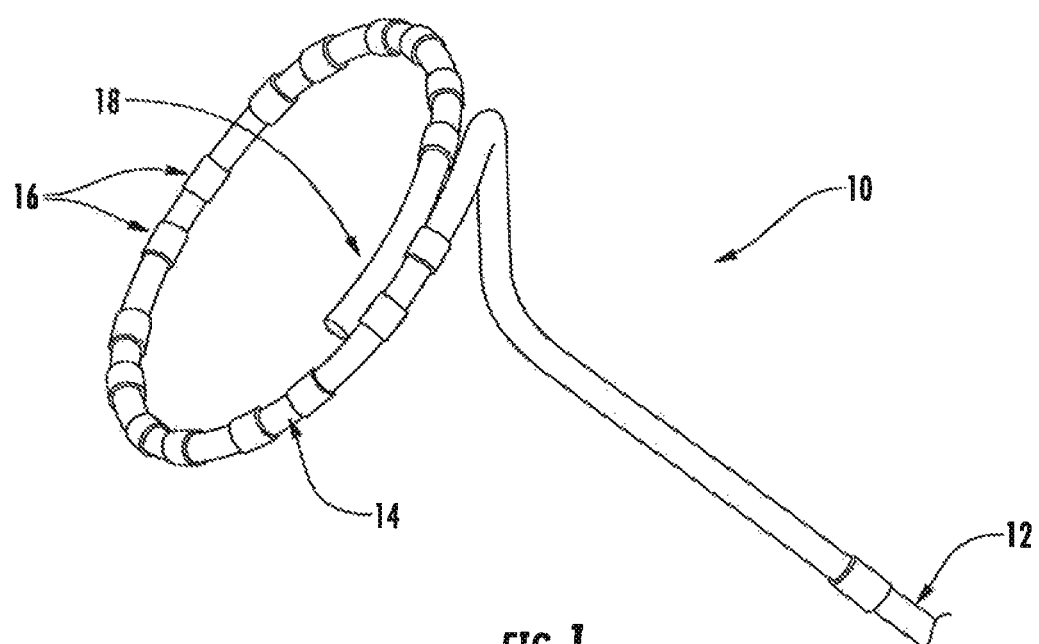
FIG. 1 is a perspective view of a prior art mapping catheter with a mapping loop at the distal end portion of an elongated shaft.
Figure 2:
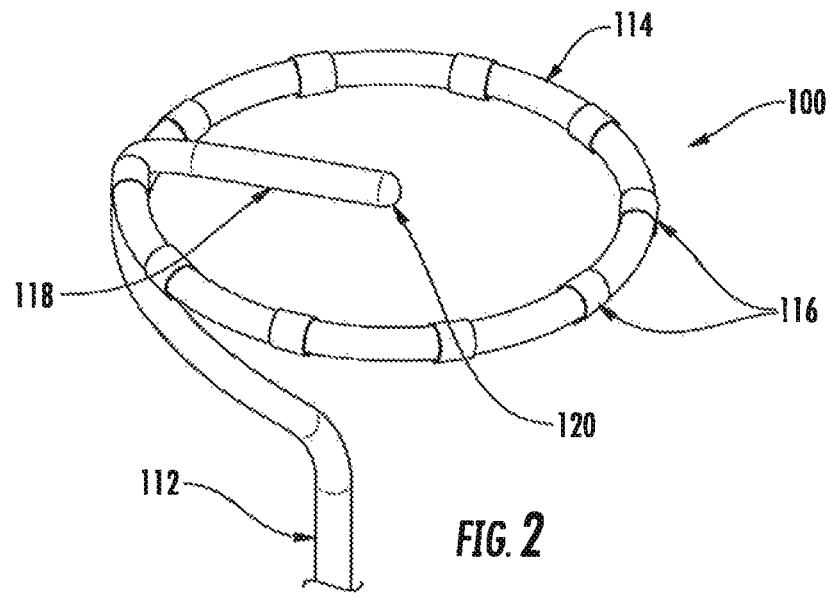
FIG. 2 is a perspective view of the distal end portion of the mapping catheter of the subject invention.
Figure 3:
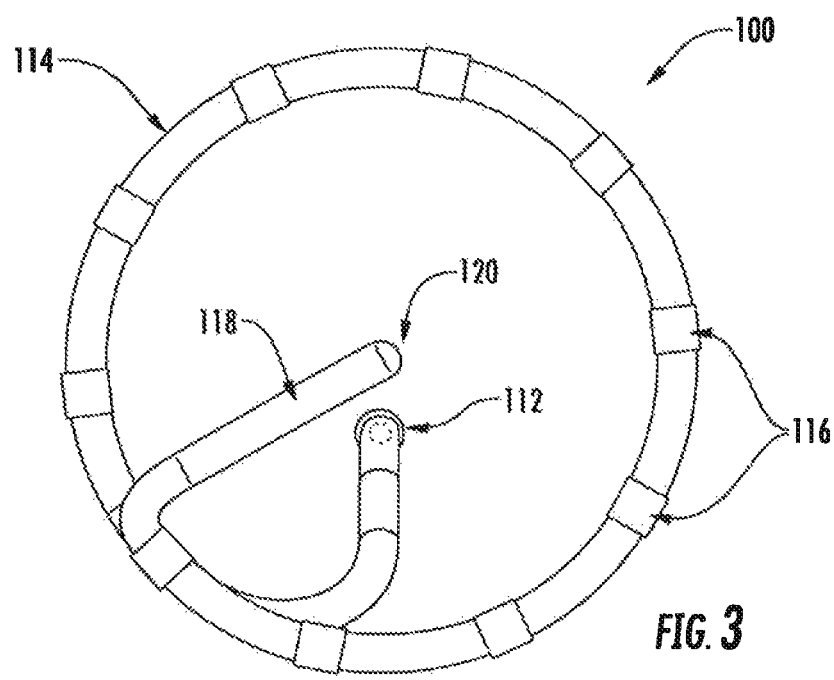
FIG. 3 is a front end view of the distal end portion of the mapping catheter of the subject invention.
Figure 4:
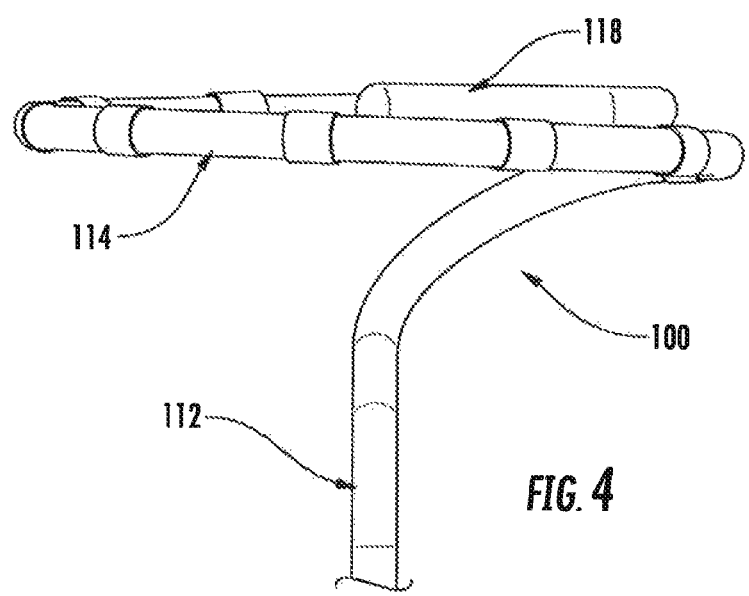
FIG. 4 is a side elevational view of the distal end portion of the mapping catheter of the subject invention.
Figure 5:
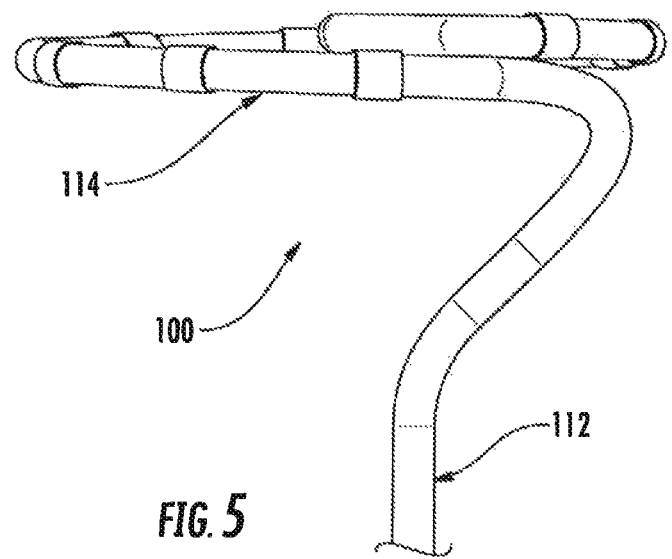
FIG. 5 is a side elevational view of the distal end portion of the mapping catheter of the subject invention, rotated 180 degrees from the view of FIG. 4.

Referring now to the drawings wherein like reference numeral identify similar or related structural features or aspects of a particular apparatus or device disclosed herein, there is illustrated in FIG. 1 a prior art mapping catheter 10. Mapping catheter 10 has an elongated body portion or shaft 12. A mapping loop 14 is operatively associated with the distal end portion of the shaft 12. The mapping loop 14 has a plurality of spaced apart mapping electrodes or bands 16 and a curved distal tip section 18 that extends about the periphery of the loop. Consequently, when the prior art mapping loop 14 is inserted into the pulmonary vein for mapping and the catheter shaft 12 is rotated counter-clockwise, the tip section 18 of the mapping loop 14 can catch onto, and perforate the pulmonary vein.

Referring now to FIGS. 2 through 5, there is illustrated an electro-physiology mapping catheter constructed in accordance with a preferred embodiment of the subject invention and designated generally by reference numeral 100. The electro-physiology mapping catheter 100 includes an elongated body 112 having opposed proximal and distal end portions and defining a longitudinal axis therebetween. A distal end portion of the elongated body 112 includes a generally circular mapping loop 114 that extends through a plane oriented generally perpendicular to the longitudinal axis of the elongated body 112. In accordance with the subject invention, the circular mapping loop 114 has an inwardly bent distal tip section 118.

The inwardly bent distal tip section 118 is bent radially inward toward a center of the circular mapping loop 114. The inwardly bent distal tip section 118 is lying generally within the plane of the circular mapping loop 114. The circular mapping loop 114 has an arcuate length that is greater than about 360 degrees. More particularly, the circular mapping loop 114 has an arcuate length that is less than about 450 degrees.

Figure 6:
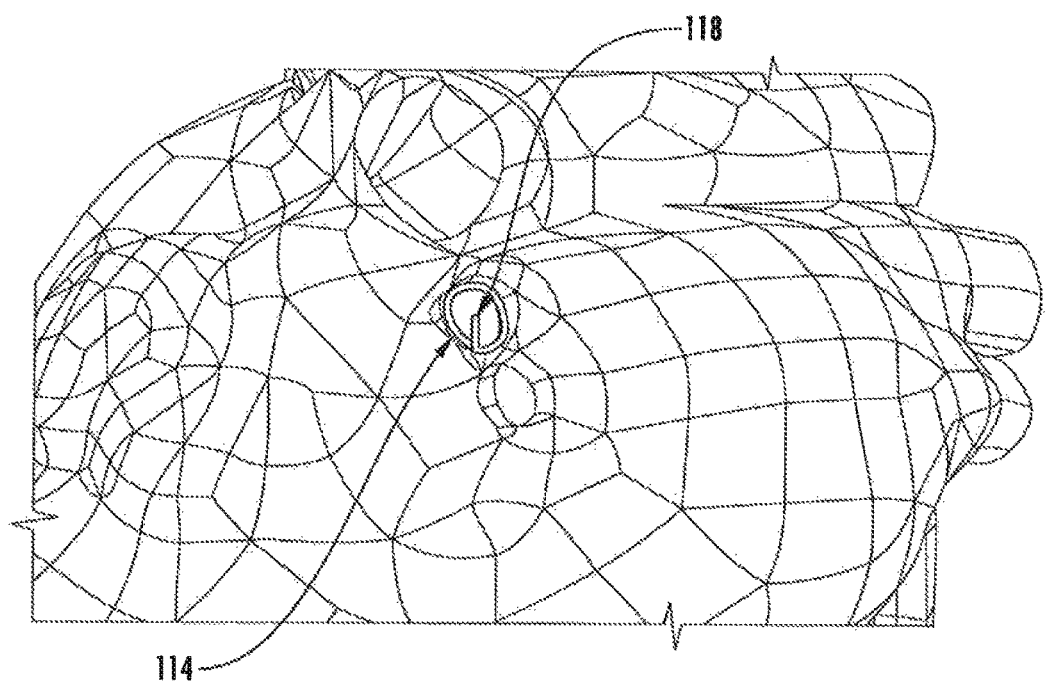
FIG. 6 is a graphical representation of a heart in which the mapping catheter of the subject invention is positioned within the pulmonary vein of the heart.

The circular mapping loop 114 includes a plurality of circumferentially spaced apart electrode bands 116. Temperature sensors can also be positioned around the circular mapping loop such that the catheter can be used for recording, mapping, stimulation or ablation. The inwardly bent distal tip section 118 of the mapping loop 114 includes an atraumatic or blunt distal tip 120. The bent distal tip section 118 generally defines a radius of the circular mapping loop 114 with the blunt distal tip positioned at a central area of the mapping loop 114. A central bore extends through the body 112 of the catheter 100 from the proximal end thereof toward the distal end thereof to accommodate a stylet for maintaining the circular mapping loop 114 in a generally straightened configuration during vascular introduction. An example of a stylet and lumen can be found is U.S. Pat. No. 7,421,295, which is incorporated herein by reference in its entirety. A handle assembly is operatively associated with the proximal end portion of the catheter body 112 for manipulating the device 100. An example of a handle assembly is shown and described in U.S. Pat. No. 9,061,120, which is incorporated herein by reference in its entirety, In use, when the mapping catheter loop 114 is positioned within the pulmonary vein as shown in FIG. 6, counter-clockwise rotation of the loop 114 will not present contact of the tip section 118 to the pulmonary vein, thereby preventing pulmonary vein perforation. Moreover, the tip section 118 is protected by the surrounding loop 114 from pulmonary vein contact. The extension of the tip section 118 to the center of the loop 114 also reduces the strength of the tip of the loop comes into contact with heart tissue in a flat, face forward orientation. Moreover, if this occurs, the tip section 118 will deflect away and not penetrate the heart tissue.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. An electro-physiology mapping catheter for insertion within a heart comprising:
    a) an elongated body having opposed proximal and distal end portions and defining a longitudinal axis therebetween;
    b) a generally circular mapping loop operatively associated with the distal end portion of the body, the mapping loop extending through a plane oriented generally perpendicular to the longitudinal axis of the elongated body, and having a distal tip section bent radially inward toward a center of the circular mapping loop, wherein the distal tip section includes an atraumatic tip positioned in a central area of the circular mapping loop within the plane of the mapping loop, wherein the mapping loop includes a plurality of circumferentially spaced apart electrode bands, and wherein the distal tip section extends along a radius of the mapping loop.

2. An electro-physiology mapping catheter as recited in claim 1, wherein the circular mapping loop has an arcuate length that is about 450 degrees.

* * * * *